US008013189B2

(12) United States Patent
Burkhardt et al.

(10) Patent No.: US 8,013,189 B2
(45) Date of Patent: Sep. 6, 2011

(54) ACCELERATED AMIDE AND ESTER REDUCTIONS WITH AMINE BORANES AND ADDITIVES

(75) Inventors: Elizabeth Burkhardt, Bridgeville, PA (US); Alex J. Attlesey, Cranberry Township, PA (US); Christopher P. Sutton, Cranberry Township, PA (US); Karl Matos, Pittsburgh, PA (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 11/859,377

(22) Filed: Sep. 21, 2007

(65) Prior Publication Data

US 2009/0082599 A1 Mar. 26, 2009

(51) Int. Cl.
C07C 209/30 (2006.01)
C07C 209/24 (2006.01)
C07C 29/136 (2006.01)

(52) U.S. Cl. ......... 564/489; 564/498; 568/880; 568/884

(58) Field of Classification Search ................. 564/489, 564/498; 568/880, 884
See application file for complete search history.

(56) References Cited

U.S. PATENT DOCUMENTS

| 6,204,405 | B1 * | 3/2001 | Brown | 558/288 |
| 6,218,585 | B1 | 4/2001 | Matos et al. | |
| 6,610,894 | B2 * | 8/2003 | Matos et al. | 568/814 |
| 7,767,833 | B2 * | 8/2010 | Potyen et al. | 549/213 |
| 2006/0241298 | A1 | 10/2006 | Mortko et al. | |
| 2009/0082568 | A1 * | 3/2009 | Burkhardt | 546/13 |

FOREIGN PATENT DOCUMENTS

| FR | 2824830 A1 | 11/2002 |
| GB | 917006 A | 1/1963 |
| WO | WO-2004/092126 A2 | 10/2004 |
| WO | WO-2005/087719 A1 | 9/2005 |
| WO | WO-2007/030721 A2 | 3/2007 |
| WO | WO-2007/119106 A2 | 10/2007 |

OTHER PUBLICATIONS

Salunkhe et al., Tetrahedron Letters, vol. 38(9), 1997, p. 1519-22.*
Brown et al., "Selective Reductions. 29. A Simple Technique to Achieve an Enhanced Rate of Reduction of Representative Organic Compounds by borane-Dimethyl Sulfide", *J. Org. Chem.*, vol. 47, pp. 3153-3163 (1982).
Sessler, et al., "Synthesis and Structural Characterization of Lanthanide(III) Texaphyrins", *Inorg. Chem.*, vol. 32, pp. 3175-3187 (1993).
Bonnat, et al., "Effect of the Termperature on the Stoichiometry of borane dimethyl Sulfide Reduction of Secondary and Tertiary Amides", *Synthetic Communications*, vol. 21 (15 & 16), pp. 1579-1582 (1991).
Brown, et al., "Molecular Addition Compounds. 11. N-Ethyl-N-isopropylaniline-Borane, A Superior Reagent for Hydroborations and Reductions", *J. Org. Chem.*, vol. 63, pp. 5154-5163 (1998).
Salunkhe, et al., "N,N-Diethylaniline-Borane, an Efficient Reducing Agent for Reduction of Representative Functional Groups", *Tetrahedron Letters*, vol. 38, No, 9, pp. 1519-1522 (1997).
Brown et al., "Molecular Addition Compounds. 15. Synthesis, Hydroboration, and Reduction Studies of New, Highly Reactive tert-Butyldialkylamine-Borane Adducts", *J. Org. Chem.*, vol. 64, pp. 6263-6274 (1999).
Aldrichimica ACTA, vol. 35, No. 2 (2002).
Brown, et al., "Improved Procedure for Borane-Dimethyl Sulfide Reduction of Tertiary and Secondary Amides in the Presence of Boron Trifluoride Etherate", *Synthesis*, pp. 996-997 (1981).
Cho et al., "Catalytic Enantioselective Reactions. Part 15. Oxazaborolidine-Catalyzed Asymmetric Reduction of α-Keto Acetals with N,N-Diethylaniline-Borane (DEANB) Complex", Bull. Korean Chem. Soc., vol. 20, No. 4, pp. 397-399 (1999).

* cited by examiner

*Primary Examiner* — Yong Chu
(74) *Attorney, Agent, or Firm* — Connolly Bove Lodge & Hutz LLP

(57) ABSTRACT

In a process for the accelerated reduction of organic substrates, selected from the group consisting of esters, amides, nitriles, acids, ketones, imines or mixtures thereof, they are reacted with an amine borane, sulfide borane or ether borane complex as a borane source in the presence of organic accelerator compounds containing either Lewis acidic or Lewis basic sites in their structure, of which the Lewis acidic site can coordinate with the carbonyl or nitrile or imine group of the substrate or the Lewis basic site can coordinate with the borane.

10 Claims, No Drawings

ACCELERATED AMIDE AND ESTER REDUCTIONS WITH AMINE BORANES AND ADDITIVES

FIELD OF THE INVENTION

The present invention relates to new methods to accelerate the reduction of organic substrates like esters and amides using boranes like amine boranes with catalytic amounts of additives.

BACKGROUND OF THE INVENTION

The reduction of organic substrates, e.g. an ester, acid or ketone to an alcohol and an amide, nitrile or imide to an amine is a key transformation for the development of pharmaceutical drugs such as antibacterials, HIV inhibitors and ocular hypertension drugs. These transformations are difficult to complete selectively in the presence of other sensitive reducible functional groups. The introduction of new methods for the reduction of these organic substrates, especially of esters and amides is highly desirable.

Amine borane complexes are very stable borane sources. The borane complexes of amines are easily used on a large scale but generally less reactive than borane complexes of ethers or sulfides. Some amine boranes are even stable to aqueous solution over extended periods of time. Their applications in organic synthesis have been limited due to their low reactivity toward functional groups. In contrast to other more reactive borane complexes such as borane tetrahydrofuran (BTHF) or dimethylsulfide borane (DMSB), acidic conditions or elevated temperatures are normally required in reductions with amine boranes. Pyridine borane and trimethylamine borane are often insufficiently reactive to accomplish the amide reduction. Borane derivatives of dialkylanilines and sterically hindered amines are significantly more reactive than other amine boranes but still require prolonged heating at elevated temperatures to drive the amide reduction to completion, see Brown, H. C.; Kanth, J. V. B.; Zaidlewicz, M. *J. Org. Chem.* 1998, 63(15), 5154-5163. Salunkhe, A. M.; Burkhardt, E. R. *Tetrahedron Letters* 1997, 38(9), 1519; Brown, H. C.; Kanth, J. V. B.; Dalvi, P. V.; Zaidlewicz, M. *J. Org. Chem.* 1999, 64(17), 6263-6274. Kanth, J. V. B. *Aldrichimica Acta* 2002, 35, 57. Burkhardt and Salunkhe reported that N,N-diethylaniline borane (DEANB) efficiently reduced a variety of functional groups such as aldehydes, ketones, carboxylic acids, esters and tertiary amides at elevated temperature. Esters and hindered ketones required extensive reaction time at reflux in THF to drive the reaction to completion. These examples demonstrated lower reactivity of DEANB versus BTHF and DMSB, see Bonnat, M.; Hercouet, A.; Le Corre, M. *Synthetic Communications* 1991, 21(15-16), 1579-82. However, due to the thermal ether cleavage of BTHF and the stench of DMSB, high volume use of these borane reagents for ester and amide reductions is limited.

The reduction of the ester functionality with borane complexes requires harsh conditions, generally requiring refluxing conditions to effectively push the reduction to completion. Several examples exist using BTHF or DMSB for this purpose, see Sessler, J. L. et al. *Inorg. Chem.* 1993, 32, 3175 and Brown, H. C.; Choi, Y. M.; Narasimhan, S. *J. Org. Chem.* 1982, 47(16), 3153-63. When DMSB is used, the dimethyl sulfide is usually distilled from the refluxing solution to drive the reduction to completion. For example, selective reduction one ester of L-maleic acid dimethylester using DMSB successfully produced 3(S)-4-dihydroxybutyric acid methyl ester. Amine boranes generally do not reduce the ester functionality. However, due to the thermal ether cleavage of BTHF and the stench of DMSB, high volume use of these borane reagents is limited. Clearly, new methods must be developed for ester reductions.

The reduction of tertiary amides is generally faster than secondary or primary amides. To reduce the amide to amine, five hydride equivalents are required. Two of the hydrides are used to reduce the amide to amine and the other three hydrides are utilized to form the amine borane complex. Alternatively, $BF_3$ (one equivalent relative to substrate) can be added to complex the amine and lower the amount of borane required for the reduction to ⅔ of a mole "$BH_3$" per mole of substrate, see Brown, H. C.; Narasimhan, S.; Choi, Y. M. *Synthesis* 1981, (12), 996-7.

As discussed above, one equivalent of $BF_3$ has been used to decrease the amount of borane used in amide reductions with BTHF. But the concept of adding boron trifluoride in a catalytic amount has not been tested as a Lewis acid accelerator for the amide reduction. Furthermore, the use of $BF_3$ or other Lewis acids to activate esters toward reduction has not been addressed in the current literature.

SUMMARY OF THE INVENTION

The object of the present invention is to provide new methods to accelerate the reduction of organic substrates like esters and amides using boranes, e.g. amine boranes, with catalytic amounts of additives.

The object is achieved by a process for the accelerated reduction of organic substrates, selected from the group consisting of esters, amides, nitrites, acids, ketones, imines or mixtures thereof, by reacting with an amine borane, sulfide borane or ether borane complex as a borane source in the presence of organic accelerator compounds containing either Lewis acidic or Lewis basic sites in their structure, of which the Lewis acidic site can coordinate with the carbonyl or nitrile or imine group of the substrate or the Lewis basic site can coordinate with the borane.

Preferably, esters, acids and ketones are reduced to give alcohols, and amides, nitrites and imines are reduced to give amines.

Preferably, the amine borane, the sulfide borane and the ether borane are derived from amines, sulfides and ethers which conform to the formulae

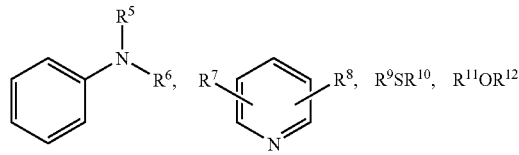

wherein $R^5$-$R^{12}$ independently are $C_{1-6}$-alkyl, phenyl, or in which each two of $R^5$ and $R^6$, $R^9$ and $R^{10}$, $R^{11}$ and $R^{12}$ independently can together also form an $C_{4-6}$-alkylene group, and $R^5$-$R^{12}$ can be substituted by halogen and $R^7$,$R^8$ can be hydrogen.

In the specification and claims, "alkyl" and "alkylene" can be linear or branched alkyl or alkylene.

Preferably, the amine borane is a tertiary amine borane, especially N,N-diethylaniline (DEANB), DMSB and BTHF being less preferred, especially when the organic accelerator compound is a Lewis basic sulfide, sulfoxide or tertiary amine.

Preferably, the organic substrate contains 4 to 30 carbon atoms.

Preferably, the organic substrate contains one or more of alkyl, aryl, aralkyl, alkaryl heterocycloalkyl, and heteroaryl groups besides the ester, amide, nitrile, acid, keto or imino functional group and may contain other functional groups not reduced by borane.

Preferably, the esters, amides, nitriles, acids, ketones and imines conform to the formulae

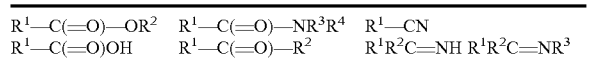

wherein
$R^1$-$R^4$ independently are $C_{1-12}$-alkyl $C_{6-12}$-aryl, $C_{7-12}$-aralkyl, $C_{7-12}$ alkaryl.

Preferably, the organic accelerator compound containing a Lewis acidic site is selected from the group consisting of Lewis acidic boron, titanium or zinc compounds or complexes. Preferably, the organic accelerator compound containing Lewis acidic sites is selected from the group consisting of $BF_3$, $BF_3$ etherate and boron compounds or complexes containing phenylene groups which can be substituted by alkyl or halogen.

Preferably, the organic accelerator compound containing Lewis basis sites is selected from the group consisting of Lewis basic sulfides, sulfoxides and tertiary amines in which case the borane source is an amine borane. Preferably, these compounds are different from the amine borane listed above.

Preferably, the tertiary amines are sterically hindered and the amines, sulfides and sulfoxides contain $C_{1-12}$-alkyl, $C_{6-12}$-aryl, $C_{7-12}$-alkaryl or $C_{7-12}$-aralkyl groups, which in the case of amines and sulfides can also form a ring structure which may include O, S or N as heteroatoms.

Preferably, the tertiary amine contains at least one, (according to one embodiment of the invention), at least two residues selected from the group consisting of phenyl which can be substituted and branched alkyl.

Especially preferred accelerator compounds are listed in the examples.

Preferably, the amount of accelerator compound, based on the amine borane, sulfide borane or ether borane is 0.01 to 100 mol-%.

The object is furthermore achieved by a composition for the accelerated reduction of organic substrates, selected from the group consisting of esters, amides, nitrites, acids, ketones, imines or mixtures thereof comprising at least one amine borane, sulfide borane or ether borane complex as a borane source and at least one organic accelerator compound containing either Lewis acidic or Lewis basic sites in their structure, of which the Lewis acidic site can coordinate with the carbonyl or nitrile or imino group of a substrate or the Lewis basic site can coordinate with the borane.

The inventors have found that the reduction of organic substrates selected from esters, amides, nitriles, acids, ketones, imines, preferably esters and amides, especially esters and tertiary amides by reacting with a borane source can be accelerated by organic accelerator compounds which contain in the molecule either Lewis acidic or Lewis basic sites. The Lewis acidic site is such that it can coordinate with the carbonyl or nitrile or imino group of the substrate, and the Lewis basic site is such that it can coordinate with the borane. A person skilled in the art will immediately recognize whether a Lewis acidic site and Lewis basic site fulfils these requirements.

Without being bound by any theory, the additives are envisioned to increase the reaction rate by two divergent mechanisms, a) coordination of a Lewis acid to the carbonyl of the substrate to increase the carbocation (electrophilic) character of the carbon, or b) dynamic equilibrium of the borane coordination to the additive to facilitate interaction of the substrate with borane.

The process can be carried out in presence or in the absence of a solvent.

Accordingly, esters of the formula,

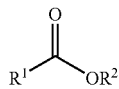

and amides of the formula,

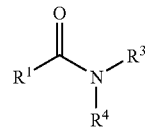

can be preferably effectively reduced with borane, complexed by amines, sulfides or ethers of the formula,

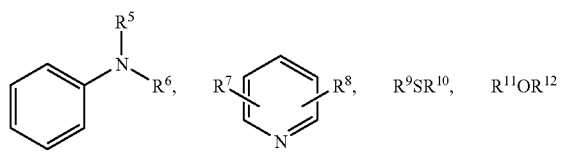

by the addition of catalytic amounts of the rate acceleration agents. These rate acceleration agents can be of the Lewis Base type, such as sulfides or hindered amines, or of the Lewis acid type, such as $BF_3$, $BF_3$-etherate, tris(pentafluorophenyl)boron, $TiCl_4$ or $ZnCl_2$, for example, such that the carbonyl of the substrate (amine or ester) can coordinate (Lewis acidic site) or the borane can coordinate (Lewis basic site).

The acceleration agent can be mixed with organic substrate, e.g. the ester or amide prior to addition of the (amine) borane or combined with the (amine) borane prior to addition to the substrate.

Furthermore, the (amine) borane and acceleration agent can be combined into a formulation to facilitate the large-scale use of the combination (formulation mixture) for the reduction of organic substrates, e.g. esters and amides. The amount of accelerator is preferably 0.01 to 20 mol-%, more preferably 0.05 to 10 mol-% relative to borane.

Another embodiment of the present invention are solutions comprising a borane complex as described, at least one of the acceleration agents (as defined) and optionally at least one solvent.

The new composition of (amine) borane (e.g. N,N-diethylaniline, 2,6-lutidine, 2-chloropyridine) with accelerator additive and preferred process of ester and amide (functional groups) reduction of the present invention can preferably be employed for transformations of esters to alcohols and amides to amines (nitrile to amine).

DETAILED DESCRIPTION OF THE INVENTION

In a preferred embodiment of the present invention the new process comprises the step of contacting an (amine) borane, an acceleration agent (catalyst) and organic substrate, e.g. an ester or amide substrate in a reaction vessel. The reaction could also be carried out easily in a continuous process.

A preferred embodiment of the present invention is where the (amine) borane and an acceleration agent (catalyst) are combined then added to an organic substrate, e.g. ester or amide substrate in a reaction vessel at the desired temperature. The formulations of the present invention generally contain the new composition of (amine) borane of the above formula with concentrations of acceleration agent between 0.0005 and 0.5 mol per mole of (amine) borane, preferably between 0.0005 and 0.2 mol per mole of (amine) borane, more preferably between 0.001 and 0.1 mol per mole of (amine) borane.

A preferred embodiment of the process of the present invention comprises the addition of an acceleration agent to the organic substrate, e.g. ester or amide prior to addition of (amine) borane to the reaction.

Another preferred embodiment of the process of the present invention comprises the addition of an (amine) borane containing the acceleration agent to the organic substrate, e.g. ester or amide in a solvent. Of course, one or more other solvents with lower complexing ability to borane than the recommended amine may also be present. Suitable solvents for the reaction solutions of the present invention are those in which the (amine) borane complexes have a high solubility. Examples are ethers like diethyl ether, 1,2-dimethoxyethane, tetrahydrofuran or 2-methyltetrahydrofuran, sulfides like dimethyl sulfide or 1,6-thioxane (these sulfides also act as borane complexing agent) and hydrocarbons like pentane, hexane(s), heptane(s), cyclohexane, toluene or xylenes. Preferred solvents for the solutions of the (amine) borane-acceleration agent formulation are tetrahydrofuran, 2-methyltetrahydrofuran, dimethyl sulfide, 1,6-thioxane, toluene, hexane(s), heptane(s) or cyclohexane, most preferred are tetrahydrofuran, 2-methyltetrahydrofuran, and toluene.

The process of the present invention can generally be carried out at a temperature of from 0 to +150° C., preferably of from 10 to 110° C. and more preferably from 20 to 85° C.

The pressure is typically ambient pressure, preferably in the range of from 0.1 to 10 bar, especially 0.5 to 2.5 bar.

Preferred accelerators according to the present invention are Lewis acidic boron, titanium or zinc compounds or complexes which contain Lewis acidic sites. A preferred boron compound is $BF_3$ or $BF_3$-etherate, triphenylborane and tris(pentafluorphenyl)borane. Furthermore, borane addition complexes of tertiary amines can be employed, in this case the tertiary amine preferably contains at least one residues selected from the group consisting of phenyl which can be substituted and branched alkyl. One example of this type of compounds are the borane complexes of aniline having a tertiary nitrogen atom. Specific examples are N-ethyl-N-isopropylaniline, N,N-diethylaniline borane (DEANB). Preferably, the accelerator compound is different from the amine borane.

Preferred organic accelerator compounds of the Lewis base type are sulfides and hindered amines for example dialkylsulfides, in which the two alkyl residues may form a cyclic residue which additionally may contain heteroatoms like N, O or S. One of this type of compounds is 1,4-thioxane. One preferably sulfide is isoamyl sulfide. It is also possible to employ dimethylsulfoxide.

Hindered amines are preferably tertiary amines which contain at least two residues selected from the group consisting of alkyl which can be substituted and branched alkyl. The third residue may be a linear alkyl. Two of the alkyl residues can form a ring structure like in piperidine. Preferred compounds are N-isopropyl-N-methyl-tert.butylamine, 1,2,2,6,6-pentamethylpiperidine, N-ethyl-N-isopropylaniline etc. Further possible compounds are known to the person skilled in the art.

The present invention is further illustrated by the examples. Preferred substrates are listed in the following examples.

PROCEDURAL EXAMPLES

Some reactions were carried out in the stainless steel 1 liter pressure reactor equipped with a ASI/Mettler React-IR for analysis. Before use, the reactor was cleaned and purged with nitrogen. The React-IR was set-up and calibrated according to the recommended manufacturer procedure before acquiring infrared spectra.

Other reactions were conducted in typical oven-dried glassware under nitrogen. Samples were withdrawn, quenched and analyzed by FT-IR or GC as described in detail below.

Procedural Example 1

Reduction of Esters and Amides at 50° C.

The reactor was charged with a solution of 200 mLs of dry THF and 0.1 mol ester or amide and heated to 50° C. under 20 psi nitrogen pressure with a back-pressure-regulator (BPR) set at 25 psi. DEANB (mols dependent on substrate) was fed subsurface at 30 psi over 1 hr maintaining a reaction temperature of 50° C. Completion of the reaction was determined by disappearance of the carbonyl stretch at (wavenumber dependent on substrate). After all data was collected and analyzed, the reaction was quenched with 50 mLs of MeOH at 7 to 10° C.

Procedural Example 2

Reduction of Esters and Amides at 85° C.

Reductions at 85° C. were carried out in a pressure vessel with 30 psi of nitrogen pressure, BPR of 35 psi, and a feed pressure of 40 psi. Concentration and addition time were the same as in procedural example 1.

Procedural Example 3

Reduction of Substrates in Glassware at 50° C.

Smaller scale screening reactions were completed in glassware. A 100 mL three-neck round bottom flask (clean oven-dried) fitted with condenser to $N_2$ bubbler, septa and thermocouple was charged with 0.05 mol ethylbutyrate or ethylbenzoate, 10 mLs THF and stirred for 15 minutes. After heating the flask to 50° C., a mixture of 0.05 mols of DEANB (with or without additive) was slowly added to the flask. To determine reduction time, 1 mL samples were hydrolyzed with 0.5 mL methanol and FT-IR spectrometry was used to monitor the disappearance of the carbonyl stretch (1734-1654 $cm^{-1}$ dependent on substrate).

Procedural Example 4

Reduction of Substrates in Glassware at 20° C.

Smaller scale screening reactions were completed in glassware. A 100 mL three-neck round bottom flask (clean oven-dried) fitted with condenser to $N_2$ bubbler, septa and thermocouple was charged with 0.05 mol ethylbutyrate or ethylbenzoate, 10 mLs THF and stirred for 15 minutes at ambient temperature, 20° C. A mixture of 0.05 mols of DEANB (with or without additive) was slowly added to the flask. To determine reduction time, 1 mL samples were hydrolyzed with 0.5 mL methanol and FT-IR spectrometry was used to monitor the disappearance of the carbonyl stretch (1734-1654 $cm^{-1}$ dependent on substrate).

Ratio of 1 equivalent of Substrate to DEANB:

| Substrate | Equivalents of DEANB |
| --- | --- |
| Ethylbutyrate | 1 |
| Ethylbenzoate | 1 |
| N,N dimethylacetamide | 1.67 |
| N-methylpropionamide | 2 |
| n-butyramide | 2.33 |
| Acetophenone | 1 |
| Propionic acid | 1.33 |
| n-heptane nitrile | 1.33 |

Examples R1, 2 to 15

The reduction of ethyl butyrate with DEANB was carried out by addition of DEANB containing an additive to the ester (1:1 mole ratio of borane to ester) at the selected temperature. Reactions were monitored by IR spectroscopy observing the disappearance of the carbonyl stretch. The results with a number of additives at 50° C. are shown Table 1. As can be seen from the table, 5 wt % $BF_3$-etherate additive worked better than most of the amine and sulfide additives. Addition of 10 and 15 wt % $BF_3$-etherate further decreased the time of reduction.

TABLE 1

Reduction of Ethyl Butyrate with DEANB and Acceleration Agents at 50° C.

| Example | Additive | Time (hrs) |
| --- | --- | --- |
| R1 | none | >98 |
| 2 | 5 wt % N-isopropyl-N-methyl-tert-butylamine | >78 |
| 3 | 5 wt % 1,2,2,6,6-pentamethylpiperidine | >78 |
| 4 | 5 wt % N-ethyl-N-isopropyl aniline | 54 |
| 5 | 5 wt % DMS | 68 |
| 6 | (Aldrich DEANB (7 wt % DMSB) | 68 |
| 7 | 5 wt % isoamylsulfide | 83 |
| 8 | 5 wt % 1,4-thioxane | >96 |
| 9 | 5 wt % $BF_3$-Etherate | 56 |
| 10 | 5 wt % $BF_3$-Etherate* | 54 |
| 11 | 10 wt % $BF_3$-Etherate | >30 |
| 12 | 15 wt % $BF_3$-Etherate | >30 |
| 13 | 15 wt % 1,4-thioxane | 65 |
| 14 | 15 wt % isoamylsulfide | 40 |
| 15 | 5 mol % pentafluorophenylborane | >24 |

*$BF_3$-Etherate added to the ester.
DMSB = dimethylsulfide borane;
DMS = dimethylsulfoxide The use of 5 wt % dimethyl sulfide, isoamylsulfide and/or N-ethyl-N-isopropylaniline as additives also shortened reaction time at 50° C. It was also noticed that by increasing the concentration of the isoamylsulfide additive to 15 wt %, the reaction was driven to completion in only 40 hours at 50° C.

Examples R16, 17 to 20

Table 2 shows the results of various amounts of boron trifluoride-etherate and sulfides in the reduction of ethylbutyrate by N,N-diethylaniline (DEANB) compared to DEANB without additives at 85° C. The overall rate of reaction was higher at 85° C. than 50° C. Even without additives, the ethyl butyrate reduction took only 9 hours. The addition of $BF_3$-Etherate to the reaction mixture showed complete reduction in only 6 hours.

TABLE 2

Reduction of ethyl butyrate with DEANB and Acceleration Agents at 85° C.

| Example | Additive | Time (hrs) |
| --- | --- | --- |
| R16 | None | 9 |
| 17 | 5 wt % DMS | 8 |
| 18 | 5 wt % isoamylsulfide | 7 |
| 19 | 5 wt % $BF_3$-Etherate | 6 |
| 20 | 5 wt % $BF_3$-Etherate in DEANB* | 7 |

*DEANB w/additive aged 90 days

Examples R21, 22, 23, 24

In contrast to ethyl butyrate reduction, the reaction of ethyl benzoate (C=O at 1725 $cm^{-1}$) with DEANB was slower regardless of the additive. Temperatures exceeding 90° C. were needed for completion. The data is summarized in Table 3.

TABLE 3

Ethyl Benzoate Reduction with DEANB (1:1 ratio of ester:amine borane) in THF

| Example | Additive | RxN Temperature (° C.) | Time (hrs) |
| --- | --- | --- | --- |
| R21 | None | 85 | >28 |
| 22 | 5% isoamylsulfide | 97* | 12 |
| 23 | 5% DMS | 85 | >24 |
| 24 | 5% $BF_3$ Etherate | 85 | >24 |

*Reaction overheated.

Those skilled in the art will appreciate that the invention described herein is subject to variations and modifications other than those specifically described herein. It is to be understood that the invention includes all such variations and modifications. The invention also includes all of the steps, features, compounds and compositions referred to or indicated in this specification, individually or collectively, and any and all combinations of any two or more of said steps or features.

While the present invention is described herein with the reference to illustrated embodiments, it should be understood that the invention is not limited to these examples. Therefore, the present invention is limited by the claims attached herein.

The invention claimed is:

1. A process for the reduction of organic substrates, selected from the group consisting of esters, amides, nitriles, acids, ketones, imines or mixtures thereof, by reacting with an amine borane as a borane source in the presence of organic accelerator compounds different from the amine borane containing Lewis basic sites in their structure, of which the Lewis basic site is available to coordinate with the borane, wherein the organic accelerator compound containing Lewis basic sites is selected from the group consisting of Lewis basic sulfides, sulfoxides and tertiary amines.

2. A process as claimed in claim 1, wherein esters, acids and ketones are reduced to give alcohols, and amines, nitriles and imines are reduced to give amines.

3. A process as claimed in claim 1, wherein the amine borane is derived from amines which conform to the formulae

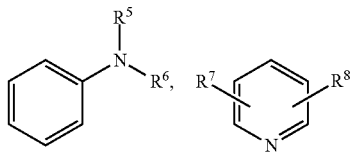

wherein $R^5$-$R^8$ independently are $C_{1-6}$-alkyl, phenyl, or in which each two of $R^5$ and $R^6$ independently can together form an $C_{4-6}$-alkylene group, and $R^5$-$R^8$ can be substituted by halogen and $R^7$, $R^8$ can also be hydrogen.

4. A process as claimed in claim 3, wherein the amine borane is N,N-diethylaniline borane (DEANB).

5. A process as claimed in claim 1, wherein the organic substrate contains 4 to 30 carbon atoms.

6. A process as claimed in claim 5, wherein the organic substrate contains one or more of alkyl, aryl, aralkyl, alkaryl, heterocycloalkyl and heteroaryl groups besides the ester, amide, nitrile, acid, keto or imino functional group and may contain other functional groups not reduced by borane.

7. A process as claimed in claim 5, wherein the esters, amides, nitriles, acids, ketones and imines conform to the formulae

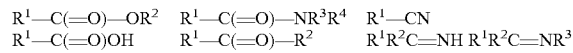

wherein
$R^1$-$R^4$ independently are $C_{1-12}$-alkyl, $C_{6-12}$-aryl, $C_{7-12}$-aralkyl, $C_{7-12}$ alkaryl, heterocycloalkyl and heteroaryl and may contain other functional groups not reduced by borane.

8. A process as claimed in claim 1, wherein the tertiary amines are sterically hindered and the amines, sulfides and sulfoxides contain $C_{1-12}$-alkyl, $C_{6-12}$-aryl, $C_{7-12}$-alkaryl or $C_{7-12}$-aralkyl groups, which in the case of amines and sulfides can also form a ring structure which may include O, S or N as heteroatoms.

9. A process as claimed in claim 8, wherein the tertiary amine contains at least one residue selected from the group consisting of phenyl, which can be substituted, and branched alkyl.

10. A process as claimed in claim 1, wherein the amount of accelerator compound, based on the amine borane is 0.01 to 100 mol-%.

* * * * *